(12) United States Patent
Genovese et al.

(10) Patent No.: US 7,504,958 B1
(45) Date of Patent: Mar. 17, 2009

(54) SYSTEM AND METHOD FOR DETECTION AND IDENTIFICATION OF AIRBORNE HAZARDS

(75) Inventors: James A. Genovese, Street, MD (US); Robert J. Pazada, Kingsville, MD (US)

(73) Assignee: The United States of America as represented by the Secretary of the Army, Washington, DC (US)

( * ) Notice: Subject to any disclaimer, the term of this patent is extended or adjusted under 35 U.S.C. 154(b) by 294 days.

(21) Appl. No.: 11/472,224

(22) Filed: Jun. 19, 2006

Related U.S. Application Data

(60) Provisional application No. 60/692,535, filed on Jun. 21, 2005.

(51) Int. Cl.
*G08B 17/10* (2006.01)

(52) U.S. Cl. ...................................... 340/632; 340/634

(58) Field of Classification Search ................. 340/632, 340/628, 634, 522; 73/23.2, 23.22, 23.31, 73/23.35

See application file for complete search history.

(56) References Cited

U.S. PATENT DOCUMENTS

| | | | | |
|---|---|---|---|---|
| 4,390,869 A | * | 6/1983 | Christen et al. | 340/632 |
| 4,831,332 A | * | 5/1989 | Rudisill et al. | 340/632 |
| 5,065,140 A | * | 11/1991 | Neuburger | 340/634 |
| 5,376,924 A | * | 12/1994 | Kubo et al. | 340/632 |
| 5,476,001 A | * | 12/1995 | Hoetzel et al. | 73/23.31 |
| 6,060,991 A | * | 5/2000 | Hsieh | 340/632 |
| 6,947,138 B2 | * | 9/2005 | Arno | 356/437 |
| 6,958,689 B2 | * | 10/2005 | Anderson et al. | 340/632 |
| 2005/0110633 A1 | * | 5/2005 | Lovell et al. | 340/632 |

* cited by examiner

*Primary Examiner*—John A Tweel, Jr.
(74) *Attorney, Agent, or Firm*—Ulysses John Biffoni

(57) ABSTRACT

Various embodiments of a system for detecting airborne hazards in a gaseous environment are disclosed. An embodiment of the system includes a plurality of sets of one or more detectors, where the detectors of each set measure different types of properties of gases, such as the color emitted when the gases are exposed to certain reagents or the ionization potential of the gases. Environmental gases enter the system and are split into a plurality of air flow streams, with each stream directed to pass through one of the sets of one or more detectors. Data from all the sets of one or more detectors is sent to a computer programmed to integrate this data in order to determine information related to the identity (e.g., the specific identity or a classification) of chemical compounds (e.g., hazardous compounds) present in the gases.

19 Claims, 9 Drawing Sheets

FIG. 7

| COMPOUND NAME | SPECIFIC DETECTION ELEMENT | POTENTIAL INTERFERENTS | OXIDATION REDUCTION POTENTIAL | COMBUSTION IN H FLAME (ION COUNT) | PH | COLORIMETRIC CROSS REACTIVITY POTENTIAL | ENVIRONMENTAL BY-PRODUCT ISSUES |
|---|---|---|---|---|---|---|---|
| AMMONIA | AMMONIA DOSIMETER | ALIPHATIC AMINES | N/A | N/A | BASIC 6 - 8 | ALKYLAMINES | NH4OH LIQUID |
| HCL | HCL DOSIMETER | NONE | N/A | N/A | ACID 2 - 4 | IS PRESENT WHEN CL IS > 50%RH | HYDROLYSIS BY PRODUCT OF CL |

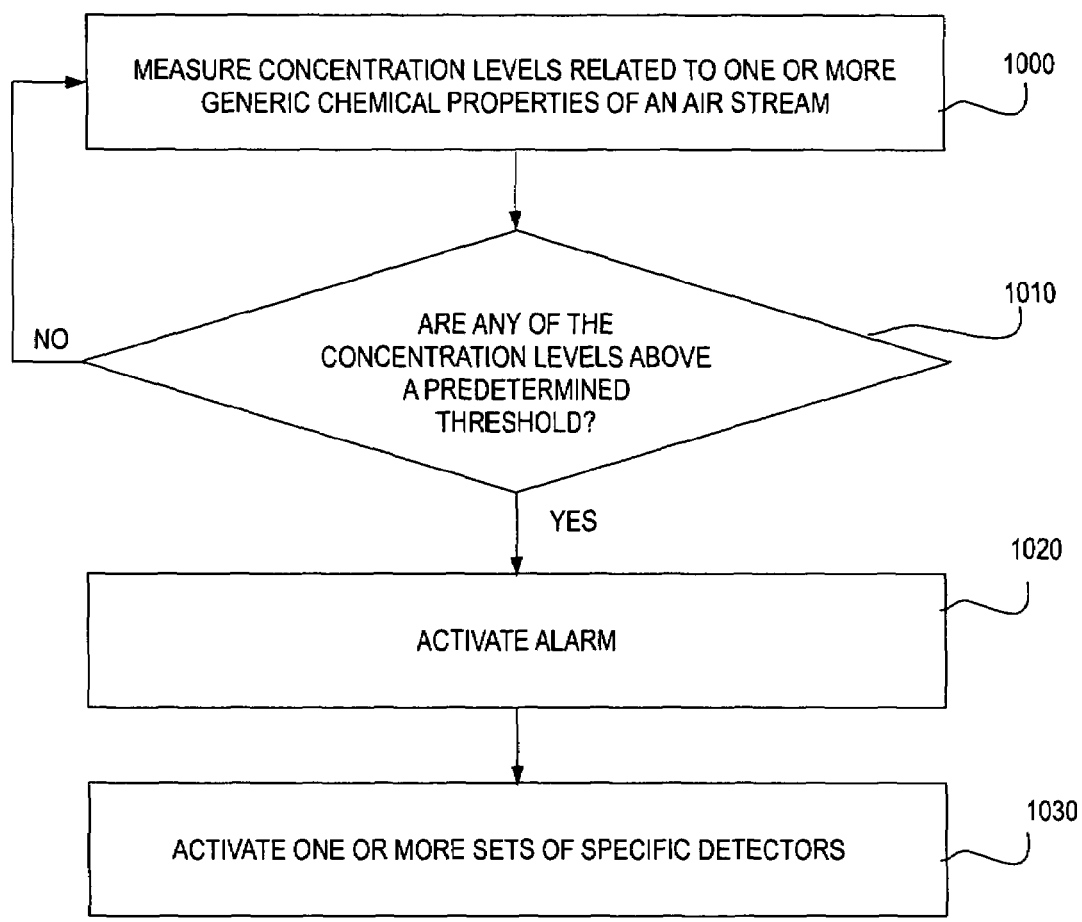

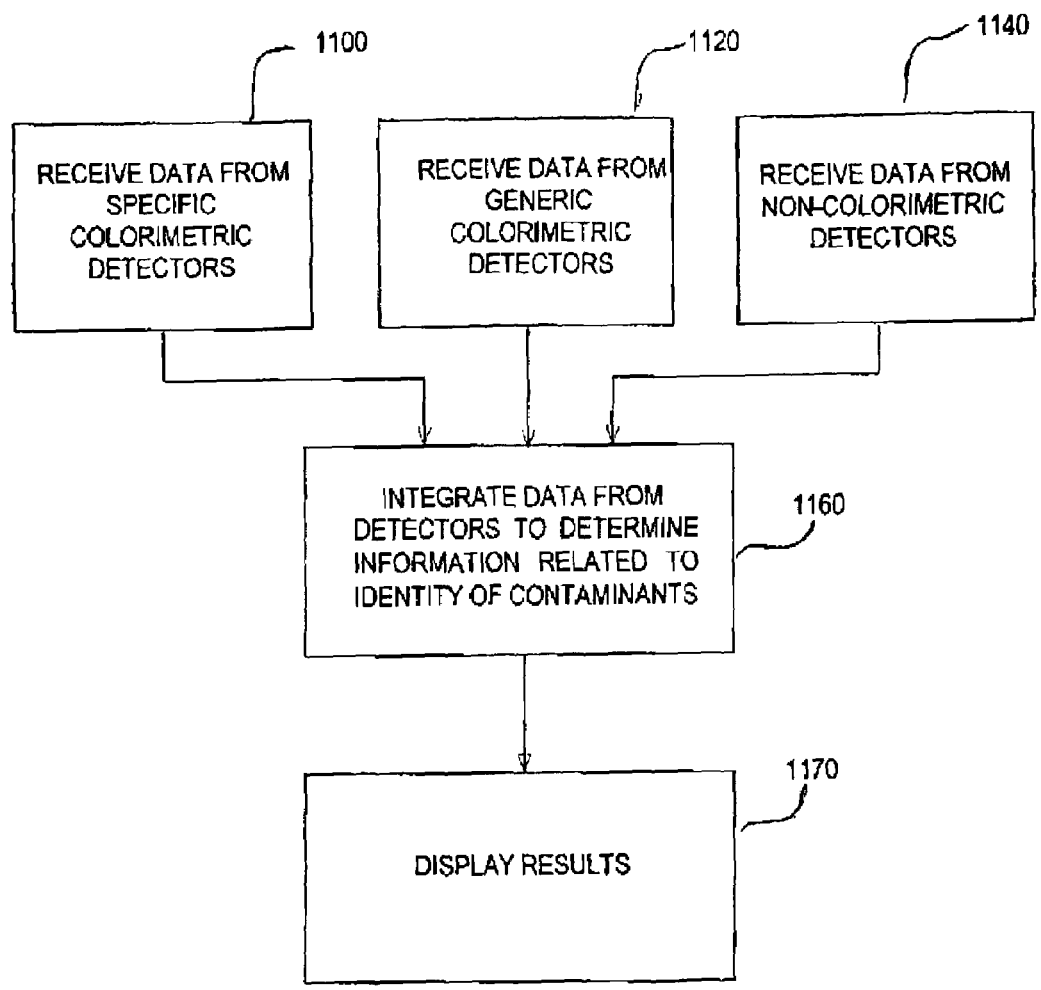

SYSTEM AND METHOD FOR DETECTION AND IDENTIFICATION OF AIRBORNE HAZARDS

RELATED APPLICATIONS

This application claims priority to U.S. Provisional Patent Application Ser. No. 60/692,535 filed on Jun. 21, 2005, which is commonly assigned.

FIELD OF THE INVENTION

The present invention relates to the field of airborne hazardous detection and identification, and in particular, to a system and method that integrates different types of detection systems to perform this identification.

BACKGROUND OF THE INVENTION

The tedious manipulation and interpretation of hazardous material detection equipment becomes problematic during actual use in field operations. Add the complication of cumbersome protective gear and a dynamic multi-component hazardous environment can create chaos in many hazardous incident response scenarios. Many of these incidents will directly challenge the user of a disparate and complex detection equipment suite. At present, there exists a wide range of chemical sensors employing a wide range of direct and indirect detection methodologies deployed to detect and identify the presence of hazardous environments. Hazardous materials teams responding to hazardous incidents and military combatants on the battlefield can be faced with an increasingly complex mixture of airborne hazards.

Most military and civilian response to these unknown hazard scenarios use an unintegrated deployment of currently fielded/marketed detectors. The chronological use, interpretation and fusion of information are in many instances ad hoc and certainly not a timely utilization of the data at hand.

SUMMARY OF THE INVENTION

An embodiment of the present invention comprises a broad-based detection system (which may be referred to below as the "Universal Detection System," or "UD System," or "UDS") that uses a unique combination and integration of sensor subsystems to detect a wide range of airborne hazards. This system employs a rigorous detection fusion algorithm that integrates sensor data to determine information related to the identity (e.g., the specific identity or classification as to the nature) of airborne vapors or aerosols.

According to an embodiment of the invention, this system comprises two main components that include a unique integration of two unique colorimetric sensors, one group chemical compound specific, the other using chemical colorimetrics to assess a disparate analysis of vapor hazards based on more fundamental physicochemical characteristics. These data will be fused in the detection/identification algorithms to determine specific ID or at least hazard family class. In some cases, where specific detection colorimetric windows are not activated due to no exposure of specific hazards, then generic chemical info from non-specific calorimetric detection windows (e.g., Redox, pH, RH, VOCs, etc.) will be used to determine possible environmental hazards and what other measures could be employed to better assess unknown hazards.

In another embodiment of the invention, this sensor integration is also used to reduce false positive detections, and characterize even non-toxic, innocuous environments.

According to an embodiment of the invention, a system for detecting airborne hazards is provided. The system includes one or more detectors for detecting first property information for gases from an environment, one or more detectors for detecting second property information for the gases, a memory storing data related to one or more known airborne hazards, and a computer for determining information related to the identity of an airborne hazard in the gases based on the first and second property information and a comparison of the first and second property information with the data stored in the memory.

According to another embodiment of the invention, the one or more detectors for detecting first property information include one or more calorimetric detectors. These may include one or more detectors capable of providing an indication of whether a specific compound is present. The one or more colorimetric detectors may also include one or more detectors that measure generic chemical properties.

According to another embodiment of the invention, the system includes a frame enclosing one or more cavities and the one or more detectors for detecting first property information comprise one or more detector windows placed within the one or more cavities of the frame. In an embodiment of the invention, at least some of the one or more detector windows include a material treated with a reagent enabling the detection of a specific compound. In another embodiment of the invention, at least some of the one or more detector windows include a material treated with a reagent enabling the detection of generic chemical properties. According to another embodiment of the invention, the frame is a plastic card. The plastic frame windows can be any appropriate size and multiple sizes can be placed on a single card.

In another embodiment of the invention, the one or more detectors for detecting second property information include one or more detectors that detect ionization potential of the gases. These may include one or more photoionization detectors. The one or more detectors that detect ionization potential may also include one or more flame ionization detectors or thermal conductivity detector (TCD).

In another embodiment of the invention, the one or more detectors for detecting second property information include one or more detectors capable of discriminating vapor/gas molecular weight and/or heat capacity such as, for example, thermal conductivity detectors ("TCDs").

According to another embodiment of the invention, the one or more detectors for detecting second property information include one or more detectors capable of determining the ability of a compound to attract electrons such as, for example, electron capture detectors ("ECDs").

In a different embodiment of the invention, a method for detecting airborne hazards is provided. According to the method, first property information for gases in an environment is received. Also, second property information for the gases is received. Finally, information related to the identity of an airborne hazard in the gases is determined based on the first and second property information and a comparison of the first and second property information with data related to one or more known airborne hazards.

In another embodiment of the invention, the first property information includes the wavelength of light emitted when the gases are exposed to a reagent.

According to another embodiment of the invention, the second property information includes the ionization potential of the gases.

In an embodiment of the invention, the action of determining information related to the identity of an airborne hazard includes determining the specific identity of the airborne hazard.

In a different embodiment of the invention, the action of determining information related to the identity of an airborne hazard comprises determining a classification for the airborne hazard.

In another embodiment of the invention, a system for detecting airborne hazards is provided. The system includes at least one computer programmed to receive first property information for gases in an environment, receive second property information for the gases, and determine information related to the identity of an airborne hazard in the gases based on the first and second property information and a comparison of the first and second property information with data related to one or more known airborne hazards.

In a different embodiment of the invention, a computer readable medium or media is provided having programming stored thereon that when executed by at least one computer causes the at least one computer to receive first property information for gases in an environment, receive second property information for the gases, determine information related to the identity of an airborne hazard in the gases based on the first and second property information and a comparison of the first and second property information with data related to one or more known airborne hazards.

In another embodiment of the invention, a method for detecting airborne hazards is provided. According to the method, the identity of gaseous chemical compounds in an environment is determined based on data received from one or more specific detectors. A confidence level is then associated with the determination of the identity of the compound. Data from one or more generic detectors as to the chemical properties found in the gases is also received. Next, it is determined whether the data received from the one or more generic detectors is synergistic with or contradictory to the determination of the identity of the compound. If the received data is determined to be synergistic with the determination of the identity of the compound, the confidence level is increased. If the received data is determined to be contradictory to the determination of the identity of the compound, the confidence level is decreased.

According to an embodiment of the invention, the action of determining whether the data received from the one or more generic detectors is synergistic with or contradictory to the determination of the identity of the compound includes comparing the received data with stored data related to one or more hazardous compounds.

In another embodiment of the invention, a system for detecting airborne hazards is provided. This system includes at least one computer programmed to determine the identity of a compound in gases of an environment based on data received from one or more specific detectors, associate a confidence level with the determination of the identity of the compound, receive data from one or more generic detectors as to the chemical properties found in the gases, determine whether the data received from the one or more generic detectors is synergistic with or contradictory to the determination of the identity of the compound, increase the confidence level if the received data is determined to be synergistic with the determination of the identity of the compound, and decrease the confidence level if the received data is determined to be contradictory to the determination of the identity of the compound.

In a different embodiment of the invention, a computer readable medium or media is provided having programming stored thereon that when executed by at least one computer causes the at least one computer to determine the identity of a compound in gases of an environment based on data received from one or more specific detectors, associate a confidence level with the determination of the identity of the compound, receive data from one or more generic detectors as to the chemical properties found in the gases, determine whether the data received from the one or more generic detectors is synergistic with or contradictory to the determination of the identity of the compound, increase the confidence level if the received data is determined to be synergistic with the determination of the identity of the compound, and decrease the confidence level if the received data is determined to be contradictory to the determination of the identity of the compound.

In a different embodiment of the invention, a method for detecting airborne hazards is provided. According to the method, a baseline is established for concentrations of an airborne hazard in a first gaseous environment where the concentration of the airborne hazard is known to be below a predetermined level. Then, it is determined whether the concentrations of the airborne hazards in a second gaseous environment exceed the established baseline.

According to another embodiment of the invention, a system for detecting airborne hazards is provided. This system includes at least one computer programmed to establish a baseline for concentrations of an airborne hazard in a first gaseous environment where the concentration of the airborne hazard is known to be below a predetermined level, and determine whether the concentrations of the airborne hazards in a second gaseous environment exceed the established baseline.

According to a different embodiment of the invention, a computer readable medium or media is provided having programming stored thereon that when executed by at least one computer causes the at least one computer to establish a baseline for concentrations of an airborne hazard in a first gaseous environment where the concentration of the airborne hazard is known to be below a predetermined level, and determine whether the concentrations of the airborne hazards in a second gaseous environment exceed the established baseline.

In another embodiment of the invention, a method for detecting airborne hazards is provided. According to the method, concentration levels related to one or more chemical properties of gases of an environment are measured. If the concentration levels exceed a predetermined threshold, one or more detectors capable of specifically identifying one or more compounds in the gases are activated.

According to another embodiment of the invention, a system for detecting airborne hazards is provided. The system includes at least one computer programmed to measure concentration levels related to one or more chemical properties of gases of an environment, and activate one or more detectors capable of specifically identifying one or more compounds in the gases if the concentration levels exceed a predetermined threshold.

According to yet another embodiment of the invention, a computer readable medium or media is provided having programming stored thereon that when executed by at least one computer causes the at least one computer to measure concentration levels related to one or more chemical properties of gases of an environment, and activate one or more detectors capable of specifically identifying one or more compounds in the gases if the concentration levels exceed a predetermined threshold.

Additional aspects of the present invention will be apparent in view of the description which follows.

DESCRIPTION OF DRAWINGS

The invention is illustrated in the figures of the accompanying drawings, which are meant to be exemplary and not limiting, and in which like references are intended to refer to like or corresponding parts.

FIG. 7 provides examples of records in a Preloaded Database of Airborne Hazards that may be used with the present invention;

FIG. 8 is a flowchart showing an operative embodiment of the present invention;

FIG. 9 is a flowchart showing another operative embodiment of the present invention.

Like reference symbols in the various drawings indicate like elements.

DETAILED DESCRIPTION

Figure 1:
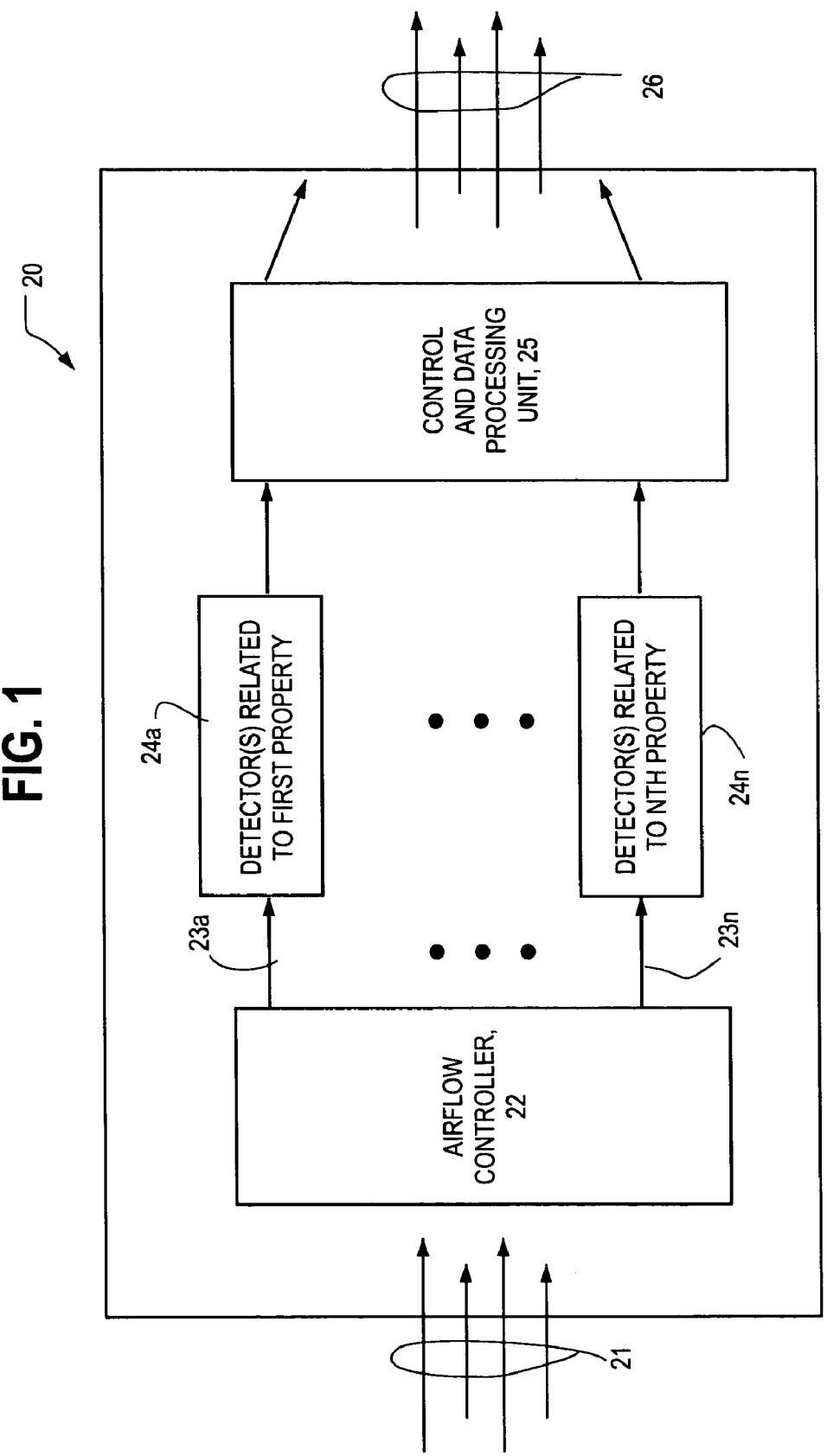
FIG. 1 is a block diagram showing an embodiment of a system of the present invention.

FIG. 1 presents a diagram that shows the components of an embodiment of the system of the present invention, which is referred to below as the Universal Detection System ("UD System" or "UDS"). Airflow Controller 22 pulls gases 21 which may contain airborne contaminants into UD System 20 and then splits the gases 21 into a plurality of air flow streams 23a through 23n. The plurality of air flow streams 23a through 23n are passed through a plurality of sets of one or more detectors 24a through 24n, where each set of one or more detectors measures different types of properties or characteristics of the gases. For example, different sets of detectors could measure the color(s) emitted when an air flow stream is exposed to certain reagents or the ionization potential associated with an air flow stream.

The detectors used by the UD System may have differing capabilities in terms of the specificity of the information they can provide regarding airborne hazards. Some detectors may be specific detectors, e.g., detectors capable of indicating only whether a specific chemical compound is present or not. Other detectors may be generic detectors, e.g., detectors that generally do not specifically identify compounds but rather provide information as to the chemical properties present in an air stream such as ionization potential, pH, oxidation-reduction potential, organic versus inorganic nature, conductivity, relative humidity and polarity. Within each set of one or more detectors, the detectors may be either all specific or generic or some combination of both.

Data from the plurality of sets of detectors 24a through 24n are sent to a computer, Control and Data Processing ("CDP") Unit 25, which integrates this data to determine information as to the nature of the gases 21. For example, CDP Unit 25 may use the integrated data to determine the specific identities (e.g., chlorine) or classifications (e.g., nerve) of contaminants in the gases 21. CDP Unit 25 also provides control over all the other components of UDS 20. Information determined by CDP Unit 25 may be presented to a user through a display (not shown). After gases are processed, they exit UDS 20 through a vent 26.

Specific examples of the components discussed above are shown in FIG. 2, which depicts another embodiment of the system of the present invention. Airborne contaminants 11 (which may be in the form of vapors or gases) are pulled into UD System 30 using fans 4 which may be governed by a fan flow controller. These fans may be small 5-volt pull-through fans that draw in external air and pull it into the UDS 30. The contaminated airflow 11 is split into two air streams 11a and 11b at the inlet end of UDS 30. Vapors processed by UDS 30 are vented through a vent 12 on the opposite side.

One flow stream 11a is directed to a set of one or more detectors that measures the color(s) emitted when the air flow stream is exposed to certain reagents. Colorimetric detection card ("CDC") 2 contains one or more detection or sensor windows, each of which may have a flat porous substrate that contains reagents. As described further below, when these reagents are exposed to specific gases or vapors, they will turn a color or change color intensity, so as to indicate the presence of a particular contaminant or provide information as to generic chemical properties (e.g., pH). It should be noted that "detector" and "sensor" are used interchangeably herein.

It may be desirable to place as many contaminant sensors on the CDC as possible. This increases detection selectivity, can improve refining identification algorithm, and detection then can be accomplished in less time. Other advantages include the ability to determine the chemical nature of the environmental hazard when specific detection is not registering or is suspect. It also may be beneficial to know all the hazards the user may not be concerned about. This is because by identifying hazards that are not present, the confidence level in the determination of the identity of a compound that has been identified is increased.

The size of the CDC may vary depending on various factors, such as the number of detection windows desired. In one example, the CDC is approximately 1.5 by 3 inches and can house as many as thirty color detection windows. Each window may have different chemical reagents that can change color when the appropriate air contaminant comes in contact with it. The frame windows can vary in size and multiple sizes can be implemented on a single card. Frame windows sizes of approximately 25 square millimeters have been employed. As discussed further below, some windows, acting as specific detectors, will have reagents to enable the specific detection of compounds, while other windows, acting as generic detectors, will have reagents to enable the detection of generic physical properties. The CDC can also contain several different types of absorbents for sample collection purposes.

Figure 3:
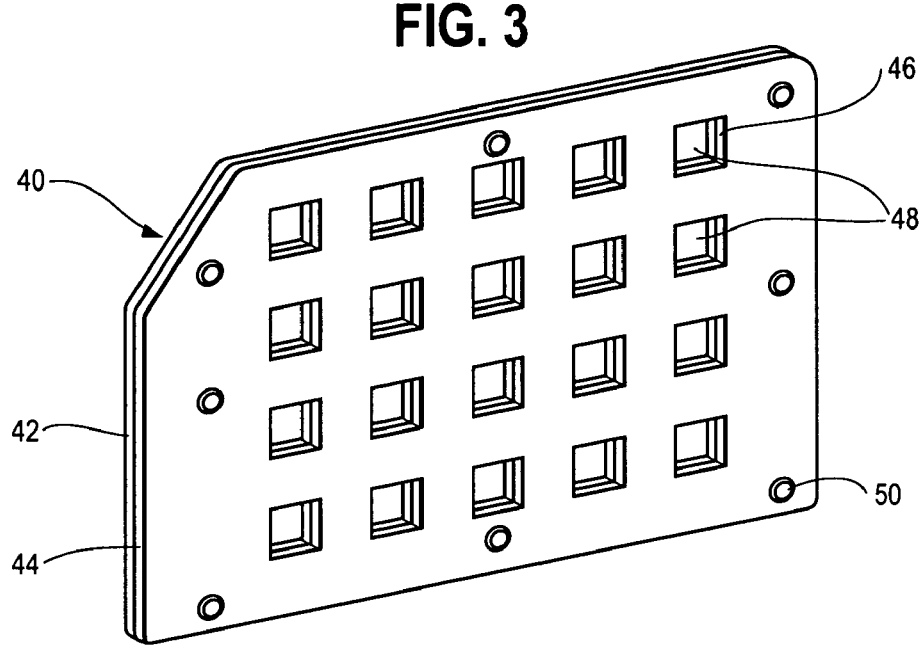
FIG. 3 is a perspective view of an exemplary calorimetric detection card that may be used in the present invention.
Figure 4:
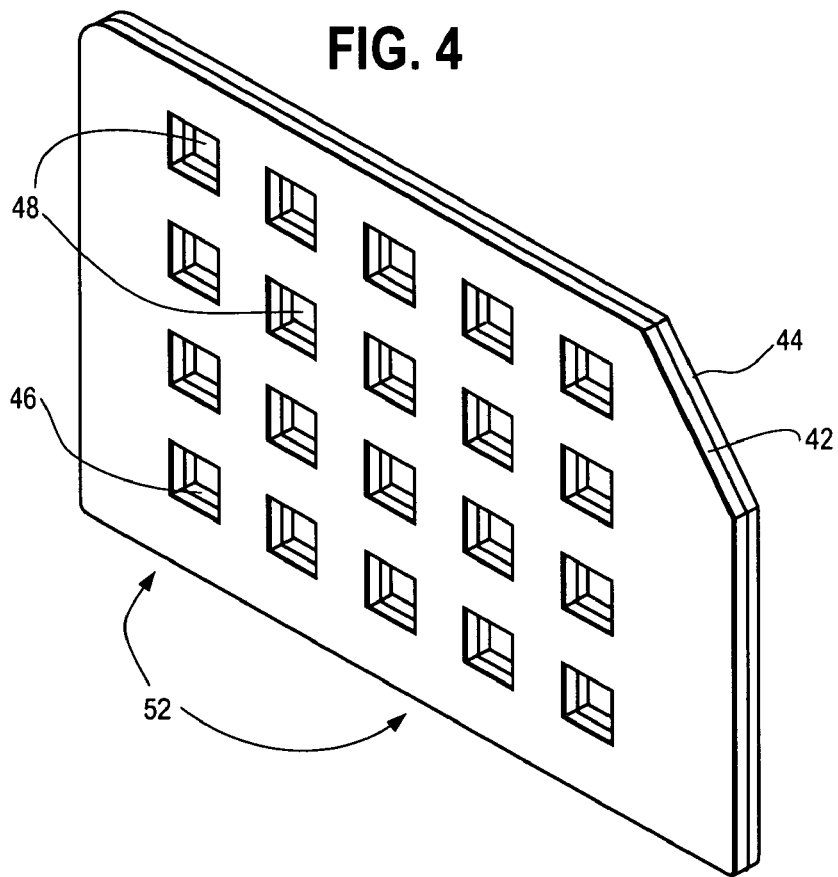
FIG. 4 is another perspective view of an exemplary colorimetric detection card that may be used in the present invention.

There are a variety of color detector card configurations that can be employed in the UDS 30, as shown in the example CDC configurations depicted in FIGS. 3-5. FIGS. 3 and 4 depict the rear view and the front view, respectively, of a color detector card with multiple detection/sensor windows or elements. The CDC of FIGS. 3 and 4 is a thin plastic card comprised of plates A (reference numeral 42) and B (reference numeral 44). These plates can be snapped together using press fit connection studs 50. FIGS. 3 and 4 also show a Keyway Bevel 40 that provides for proper insertion, sensor element cavities 46 and sensor elements 48. In FIG. 4, the arrows 52 show the perspective of image recording unit 1 (e.g., a digital camera).

Each sensor element or window may contain a solid substrate material that has been treated with the appropriate reagents to generate specific detection of compounds or generic physical properties. As discussed further below, a camera may be used to capture the color changes of the detection windows and record wavelength and intensity changes.

Figure 5B:
FIGS. 5a-5c provide additional perspective views of an exemplary calorimetric detection card that may be used in the present invention.
Figure 5A:
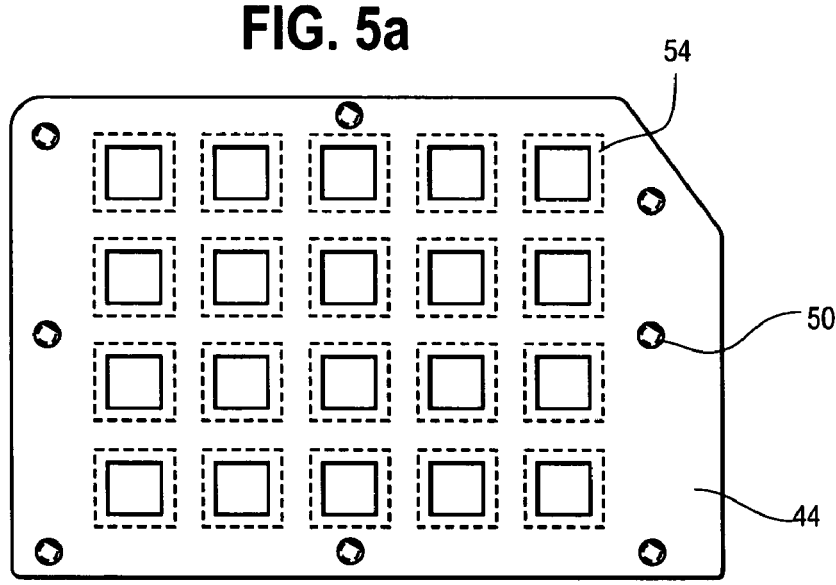
Figure 5C:

FIG. 5a shows a front view of plate B. As shown in this figure, the colorimetric substrates (either specific or generic) may be placed on sunken ledges 54 of plate B (reference numeral 44). FIGS. 5b and 5c show side views of both plates when plate A is pressed over plate B which holds sensor substrates in place when connection studs 50 are press fitted.

In one embodiment of the invention, reagent impregnated solids or liquid films deposited on solid substrates are employed.

Figure 6:
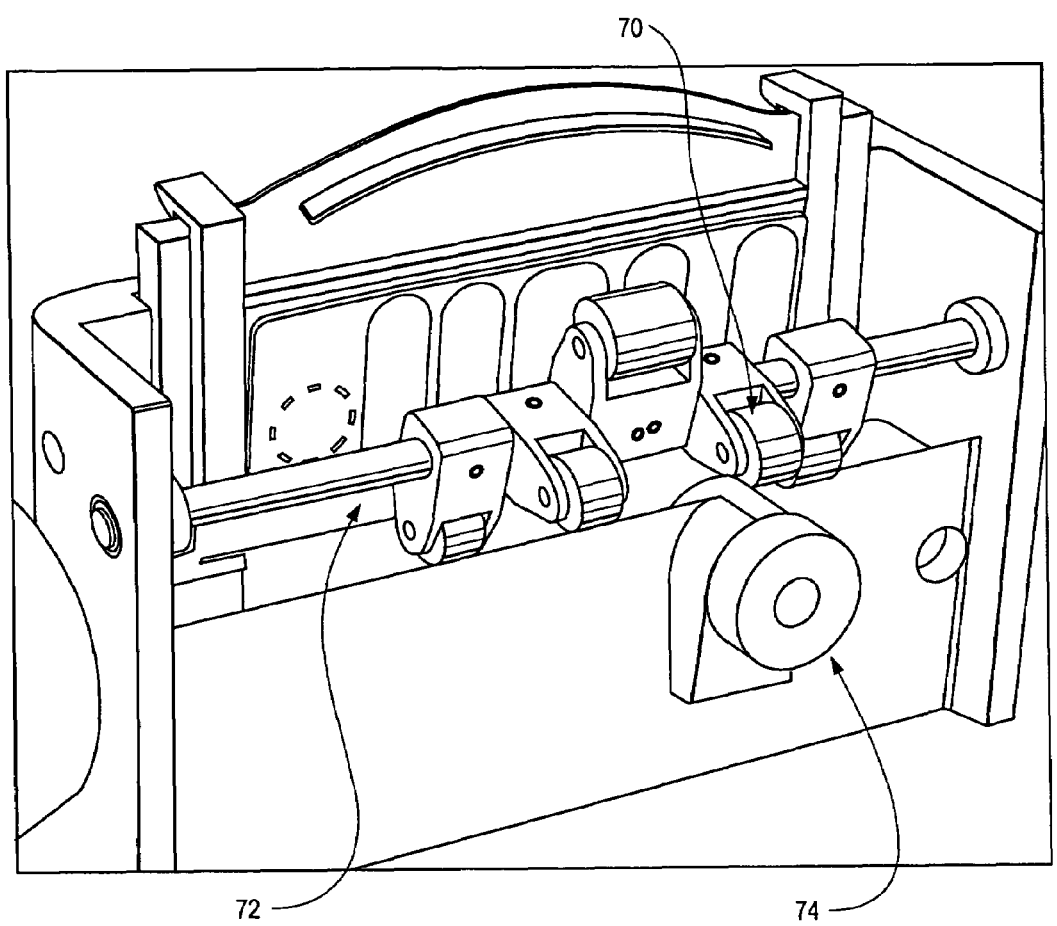
FIG. 6 is an image of an exemplary cam shaft system for breaking glass ampoules that may be used with the present invention.

However, detection of some contaminants may require the use of liquid reagents. In the case where the CDC includes glass ampoules containing liquid reagent chemistries (not shown), the UDS would include means to break or crush the glass ampoules (shown as Ampoule Breaking Mechanism 3 in FIG. 2) under the control of Control and Data Processing Unit 9, discussed below. For example, as shown in FIG. 6, this may be realized by a shaft 72 containing several cams 70 that rotate under means of a motor and motor controller system to break the reagent ampoules at the necessary time. FIG. 6 also shows an IR heater 74.

Referring again to FIG. 2, an image recording unit 1 may be positioned opposite of the color detection cards in order to record high resolution images of the multiple color changing events that can occur on the colorimetric detection card. According to an embodiment of the invention, image recording unit 1 comprises a digital color camera that contains an image sensor, utilizing Complementary Metal-Oxide Semiconductor (CMOS) technology, and a focusing lens. The image sensor may comprise a 640×480 color pixel array providing over three hundred thousand individual colorimetric elements and that allows a resolution of approximately 5 thousandths of an inch based on a single image taken of the colorimetric detection card. A higher resolution camera can be used if greater resolution is needed.

As an alternate embodiment, the digital camera can concurrently capture real time video of the detection card that can be transmitted or viewed by an external display to detect rapid or immediate calorimetric changes in any of the detection windows. The camera and Control and Data Processing Unit 9, discussed below, provide support for the following functions: light metering, white balancing, exposure control, image capture (i.e., raw or JPEG), video capture, storage of captured images or video and various camera control operations.

Figure 2:
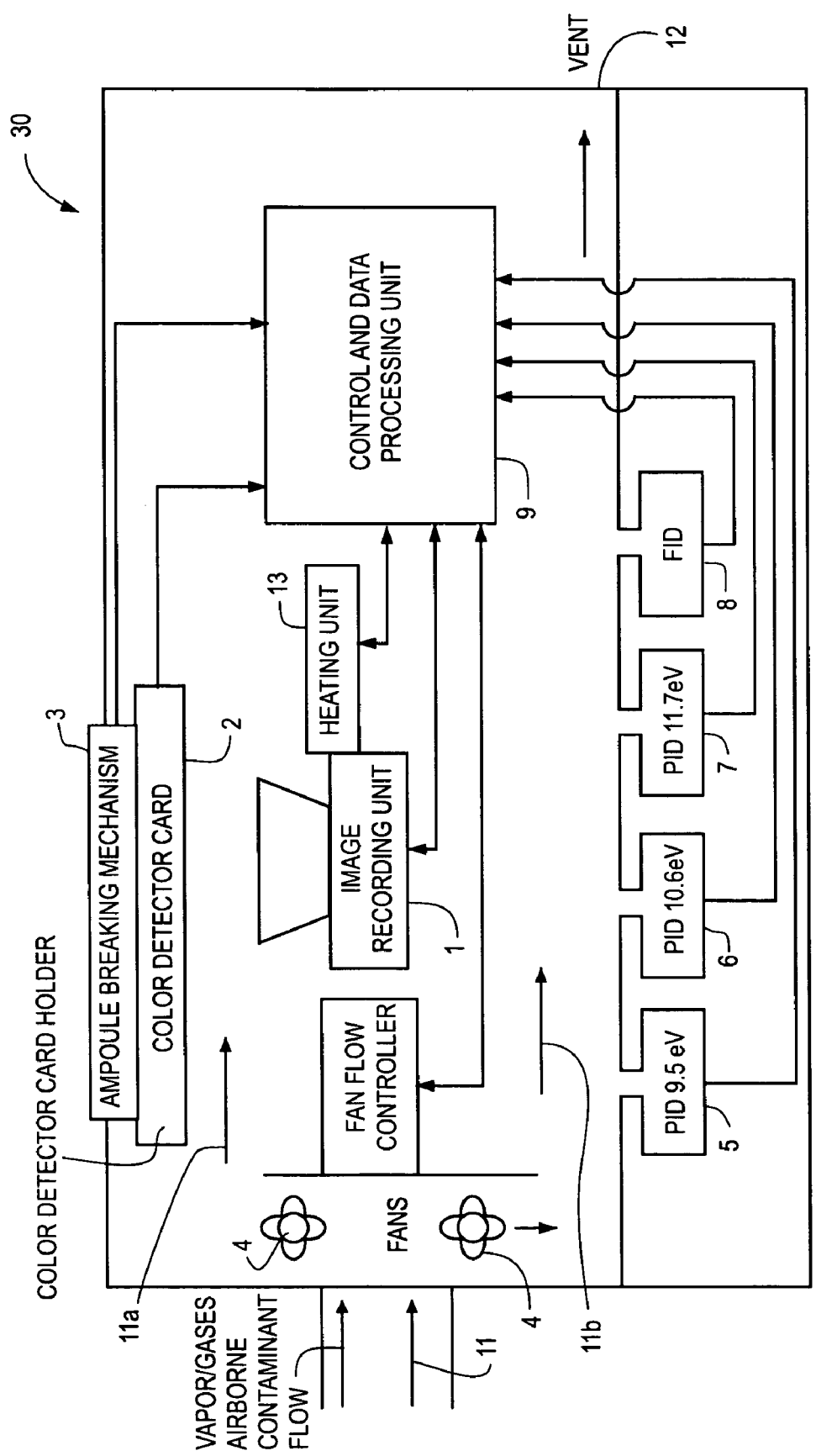
FIG. 2 is a block diagram showing another embodiment of a system of the present invention.

As shown in FIG. 2, the other flow stream 11b passes over a bank of one or more detector/sensors that measure the ionization potential of gases in order to determine different physical/chemical characteristics of the air contaminant. Some representative sensors depicted in FIG. 2 include photoionization detectors ("PIDs"), three of which (labeled with reference numerals 5, 6 and 7) are shown in the embodiment of FIG. 2, and flame ionization detectors ("FIDs"), one of which (labeled with reference numeral 8) is shown in the embodiment of FIG. 2. In the embodiment shown in FIG. 2, the PIDs have different energy ultra violet lamps, e.g., 9.5 electron volts ("eV"), 10.6 eV and 11.7 eV. The different energy UV lamps in the PIDs can ionize vapors depending on the vapor's ionization potential (IP). For the flame ionization detector 8, the vapors, if combustible in a hydrogen flame, produce ions which the FID can measure.

Although specific examples of calorimetric, photoionization and flame ionization detectors have been discussed above, it should be noted that other types of specific detectors (e.g., detectors capable of specifically identifying compounds) and generic detectors (e.g., detectors that can identify generic chemical changes in the environment) may be used with the present invention as well. For example, generic sensors such as thermal conductivity detectors ("TCDs") and electron capture detectors ("ECD") may also be used with the present invention.

It further should be noted that depending on the incident, the UDS might be used to collect a vapor sample from the airstream. This collection system will be comprised of common glass vapor sampling tubes that can easily be inserted into the flow stream to absorb vapor samples for further analyses using GC Mass Spectrometry or other known methods.

As shown in FIG. 2, UDS 30 may also include a system-heating unit 13 that controls the temperature in UDS 30 or local areas of the CDC. According to an embodiment of the invention, system heating unit 13 comprises a 4-watt infrared ("IR") heater capable of heating local areas to 120 degrees C. The IR heater may be centered within an elliptical reflector that enables heat energy to be concentrated at the incoming airflow and key areas of the calorimetric detection card that require additional heat to assist chemical reactions.

All components of UDS 30 are controlled by Control and Data Processing Unit 9. For example, CDP Unit 9 controls the internal temperature of the UDS 30 via control over heating unit 13. CDP Unit 9 also controls air flow through the UDS 30 via control over the fan flow controller. The air sampling time is adjustable through firmware download and variable based on the type of gas or vapor being detected.

In addition, CDP Unit 9 receives data from CDC 2, camera 1 and detectors 5-8 and manipulates and integrates this data according to the Universal Detection algorithm, described further below. CDP Unit 9 includes a microprocessor and a memory (e.g., RAM, ROM, PROM, EPROM or magnetic or optical storage) for storing computer code to be executed by the microprocessor to perform control and data processing functions described below.

UDS 30 also includes a database (not shown) that may be internal or external to the UDS so long as it is accessible to CDP Unit 9. This database may be preloaded with data related to various known airborne hazards which, as described below, CDP Unit 9 uses to process data received from the detectors. Some of this data may be obtained from known reliable sources. Other data may be developed empirically through lab testing of a discrete set of potential hazards.

FIG. 7 depicts an example structure of the database, which may be referred to as the Preloaded Database of Airborne Hazards. This database can be dynamically expanded during operation of the UDS to add data for additional hazards, but it may be desirable for a reasonable set of contaminants to be preloaded. In an embodiment of the invention, the data fields of the database may include some or all of the following fields, some of which are shown in FIG. 7: compound name, whether there is a specific detection element associated with it, potential interferents, ionization potentials, FID detectability, oxidation/reduction potentials, pH, hydrolysis based on ambient RH, toxicity to include LCt50s, IDLH and PEL levels, concentration data related to detection limits, molecular weight, heat capacity, hydrolysis products, chemical incompatibility and hazard class. It may be desirable for the database to be much larger than the existing number of various known threats. It may also be desirable for the database to include data for a wide range of expected environmental interferents and a select grouping of vapor generating compounds that represent a wide variety of molecular families. For example, it may be desirable for data related to Volatile organic carbons ("VOCs") to include data for hydrocarbons, unsaturated molecules and molecules that are both aliphatic and aromatic. Also, it may be desirable to include data for acids, bases, oxidizers and reducing agents.

The UDS may also include other components not shown in FIG. 2. For example, the UDS may include an additional memory, accessible to the Image Recording Unit and the CDP Unit, for storing digital images and/or video for archival and transmittal purposes. Also, the UDS may contain means for timing and control for internal illumination of the CDC. In addition, the UDS may include a user output display that presents information, such as, information as to the nature of an airborne hazard (e.g., specific identity of a compound or classification of a compound) and concentration of the hazard. Also, external communication ports (e.g., serial, parallel, USB, IR or RF) connected to the CDP Unit allow for interoperability with other critical detection systems and data transmission. In addition, the UDS may include additional measurement and detection instruments under the control of the CDP Unit such as, for example, a hygrometer and an M256 vapor-sampler.

The general operation of the UD System may now be described. The UD System of the present invention may operate in a plurality of threat modes. For example, according to an embodiment of the invention, the UD System may operate in a non-threat mode, a low threat mode, or a high threat mode. The different operational modes may be user selectable (e.g., via physical controls on the UDS, such as switches, or via commands sent to the CDP Unit through an external communication port). In addition, the CDP Unit may automatically switch the operational mode under certain circumstances, as described below.

In any of the operational modes, environmental gases and vapors are continuously pulled into the UDS (e.g., by the fans of FIG. 2) and split into a plurality of air flow streams that pass through a plurality of sets of one or more detectors (e.g., the colorimetric detection windows of the CDC and ionization detectors of FIG. 2) before flowing out of the UDS via a vent. The rate at which gases are pulled into the UDS may be adjusted depending on environmental conditions. For example, a low rate may be used to optimize detection of low concentrations of contaminants or a high rate may be used to improve mass transport. The different flow rates may be user selectable and/or automatically selected by the CDP Unit. For example, the CDP Unit could be pre-programmed to operate the UD system at a default flow rate which could then be adjusted by a user as desired. In addition, different flow rates could be automatically selected by the CDP Unit depending on the operational mode of the UD system.

Non-threat mode is intended for use in situations where the level of airborne hazards is known to be non-threatening. In non-threat mode, the UD system may use its suite of generic sensors to establish "chemical baselines" by assessing background chemicals in known safe environments. These data should also be archived to assist in establishing alarm thresholds, discussed below.

It is important to note that conventional sensors generally do not establish a chemical vapor baseline so environmental tracking becomes tedious. Most conventional sensors just establish an electronic detection background, but that background does not assess the baseline chemical nature of the environment before a toxic hazard is introduced.

In the low threat mode, only one or more generic detectors are operational. As discussed below, these generic detectors can trigger the turning on of other detector systems within the UDS. Consequently, it may be desirable to use generic detectors that have a high dynamic range as these triggering generic detectors since such generic detectors will be able to detect low or high concentrations very rapidly without their sensing mechanisms being overwhelmed and thus will be able to provide rapid initial detection of unknowns in the environment. For example, according to an embodiment of the invention, the generic detectors used as triggering generic detectors in low threat mode include the three Photoionization detectors ("PID"s), the Flame Ionization Detector ("FID") and the generic calorimetric detectors discussed above.

In low threat mode, the general operation of the UD System can be described in connection with the flowchart of FIG. 8. First, the UD System measures molecular concentration levels related to one or more generic chemical properties of an air stream, as represented in block 1000. For example, the air stream may be passed through one or more detectors (e.g., one or more of detectors 5, 6, 7, 8 and the generic detectors of CDC 2 shown in FIG. 2) that measure the molecular concentration levels related to one or more generic chemical properties such as, for example, ionization potential, pH, oxidation-reduction potential, organic versus inorganic nature, conductivity, relative humidity and polarity.

Next, the UD System determines whether any of the molecular concentration levels are above a predetermined threshold, as represented in block 1010. For example, where the chemical properties being measured include ionization potential, then the operations represented in block 1010 may determine whether the ionization potential of the gases in the air stream fall within a particular ionization potential range and whether the molecular concentration levels of the gases falls above a predetermined concentration level for that ionization potential range. The predetermined threshold or concentration level may be set at a level equal to a normally accepted background concentration as determined by, for example, the chemical baselines established in non-threat mode, as mentioned above.

For instance, if the generic detectors used in low threat mode include a plurality of PIDs each of which has a different energy lamp (as shown in FIG. 2), the unique responses of each, when combined, will provide information on ionization potential ranges of the gases in the stream. For example, as shown in FIG. 2, PID 5 ionizes compounds at 9.5 eV and all compounds whose ionization potential is at or below 9.5 eV. PID 6 ionizes all compounds whose ionization potential (IP) is at or below 10.6 eV. And PID 7 ionizes compounds at or below 11.7 eV. Thus, using the PIDs above, the UD System can separate out compounds based on ionization potential using the following selective IP bins: Compounds with IPs<9.5 eV; compounds with IPs between 9.5 eV and 10.6 eV; compounds with IPs between 10.6 eV and 11.7 eV; and finally those compounds with IPs greater than 11.7 eV.

If the generic detectors used in low threat mode include a flame ionization detector (such as FID 8 of FIG. 2), then the operations represented in block 1010 may also determine whether the gases in the air stream are combustible in a Hydrogen flame and, if so, whether the molecular concentration level (e.g., ion count) of such gases falls above a predetermined threshold.

As shown in FIG. 8, if, via the operations represented in block 1010, it is determined that the molecular concentration levels related to one or more generic chemical properties is not above the predetermined threshold, the operation of the UD System flows back to block 1000 where the UD System continues to measure molecular concentration levels in the air stream.

However, if the determination made according to the operations represented in block 1010 is positive, then an alarm is activated, as represented by the operations of block 1020. If desired such an alarm may be silent, e.g., a visual alarm.

In addition to activating an alarm when the threshold above is breached, the UD System activates one or more sets of specific detectors, as represented by the operations of block 1030. For example, if a predetermined threshold is breached, the UD System could activate the color detector card 2 (FIG. 2). Activation of specific detectors may include the activation of other systems that support those detectors. For instance, in addition to activating color detector card 2, the UD System may also activate image recording unit 1 and ampoule breaking mechanism 3 (if necessary). Activation of the specific detectors and their support systems enables the UD System to provide more information as to the nature (e.g., specific identity or a classification) of the chemical compounds present in the air stream.

As seen from the above, in the low threat mode, the UD System saves power, but is still set to detect an exceptionally large array of environmental compounds including common background interferent compounds. And if concentration levels of possible contaminants exceeds threshold levels, the UD System escalates its operating threat mode by activating additional and more specific detection systems.

In the high threat mode, all generic and specific sensor detectors in the UD System are up and running continuously. In high threat mode, the UD System uses data received from these detectors to determine information related to the identity (e.g., the specific identity or classification information) of chemical or biological compounds present in environmental gases.

FIG. 9 is a flowchart depicting an example of how the UD System of FIG. 2 may operate in high threat mode. As mentioned previously, environmental gases are pulled into the UD System by fans 4 and split into air streams that are passed through the colorimetric detectors (e.g., color detector card 2) and the non-colorimetric detectors (e.g., PIDs 5, 6 and 7 and FID 8). The calorimetric detectors (specific and generic) and the non-colorimetric detectors then concurrently obtain data from their respective air streams as discussed further below.

As represented by the operations of block 1100, Control and Data Processing ("CDP") Unit 9 receives data from the specific colorimetric detectors. As mentioned previously, each of the specific calorimetric detectors may include a reagent that when exposed to specific gases or vapors will turn color or change color intensity thereby indicating the presence of a particular contaminant. CDP Unit 9 may then control image recording unit 1 to record one or more images of the reagent for each specific calorimetric detector at appropriate sampling times. Images of the reagent for each specific calorimetric detector are compared with an optical wavelength database where values or ratios of the blue, green and red components are compared to determine whether the images of the reagent indicate that the corresponding contaminant has been detected. Also, the images may be analyzed to track the color of the pixels, the intensity of pixels, the change in the number of pixels, and the rate of pixel change over time, all of which can be used to determine molecular concentration levels.

From the images the CDP Unit 9 receives of the reagents for the specific calorimetric detectors, the CDP Unit 9 can determine how many of the multiple specific detector windows on the colorimetric detection card 2 changed, which detector windows changed and how much (e.g., molecular concentration level) compound is present.

CDP Unit 9 also receives data from the generic colorimetric detectors, as represented by the operations of block 1120 of FIG. 9. For example, CDP Unit 9 may control image recording unit 1 to obtain data from each of the generic calorimetric detectors in a similar manner as described above. The various generic colorimetric detectors enable the measurement of such generic chemical properties as pH, oxidation-reduction potential, organic versus inorganic nature, conductivity, relative humidity and polarity. Data from the generic colorimetric detectors can be used to determine molecular concentration levels in a similar manner as described above. Similar to the case of the specific colorimetric detectors, CDP Unit 9 can determine, from the images received of the reagents for the generic colorimetric detectors, how many of the multiple generic detector windows on the calorimetric detection card 2 changed, which detector windows changed and the molecular concentration levels present.

CDP Unit 9 also receives data from the generic non-colorimetric detectors, as represented by the operations of block 1140 of FIG. 9. CDP Unit 9 may obtain data from the generic non-colorimetric detectors (e.g., PIDs 5, 6, and 7 and FID S of FIG. 2) in a similar manner as described above in connection with low threat mode operation. From the data received from the PIDs and FID, CDP Unit 9 can determine what PIDs were triggered and if and how much FID signal was registered.

Data from the specific colorimetric detectors, generic calorimetric detectors and generic non-colorimetric detectors are then integrated or fused in order to determine information related to the identity (e.g., specific identify or classification) of contaminants in the air streams, as represented in the operations of block 1160 of FIG. 9.

Figure 10:
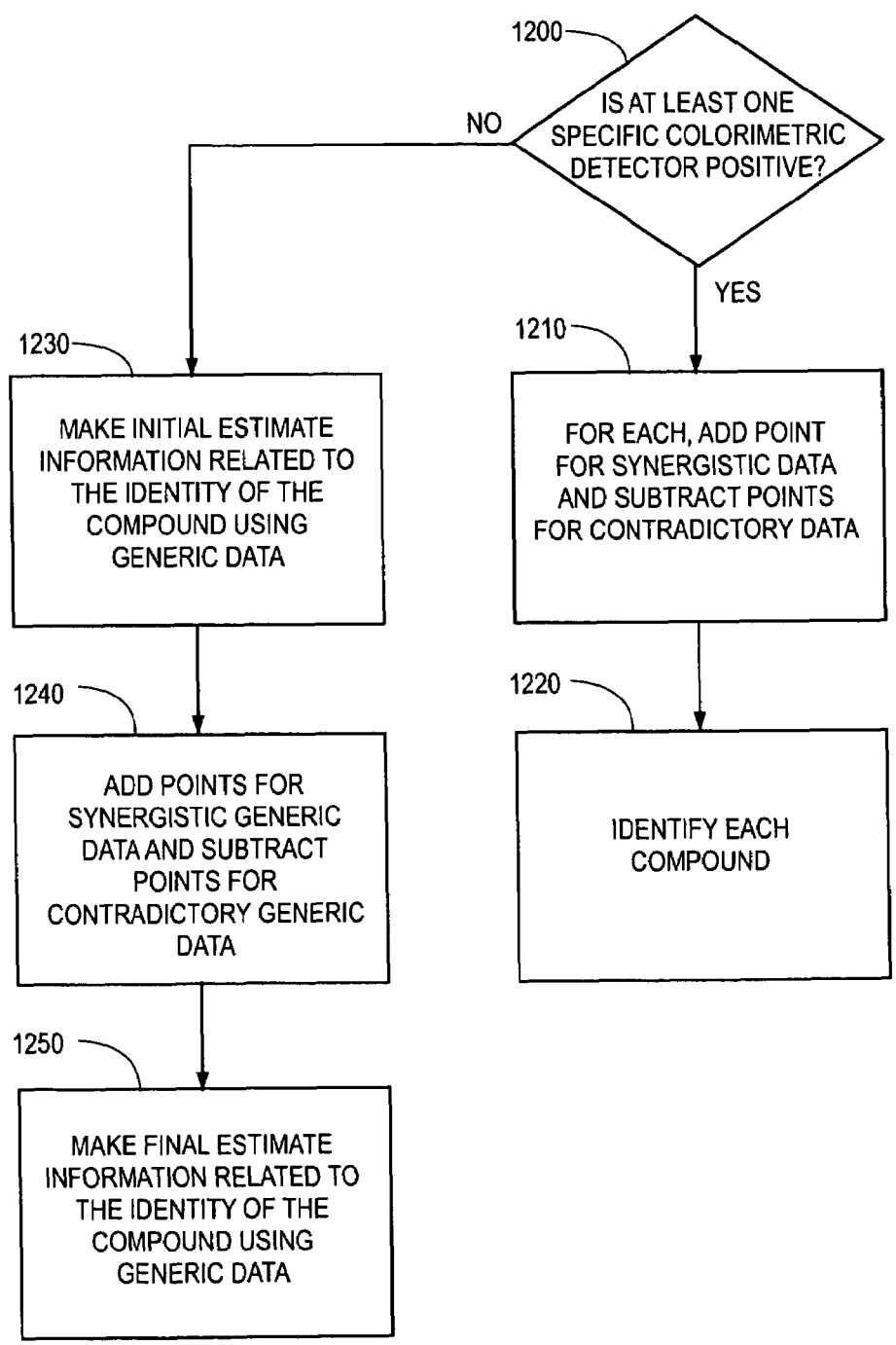
FIG. 10 is a flowchart showing a further operative embodiment of the present invention.

An exemplary method for integrating this data is depicted in the flowchart of FIG. 10. As described further below, the method shown in FIG. 10 essentially involves a score value representing the confidence of the determination of information related to the identity of a compound and increasing or decreasing the score value depending on whether data is determined to be synergistic with or contradictory to, respectively, the information related to the identity.

As shown in FIG. 10, CDP Unit 9 first determines if at least one specific colorimetric detector is positive, as represented by the operations of block 1200. For example, CDP Unit 9 determines if the reagent for at least one specific colorimetric detector has changed color or intensity to indicate the presence of the compound corresponding to that reagent.

If this determination is positive, then for each specific calorimetric detector with a positive indication, the operations represented in blocks 1210 and 1220 are performed. According to the operations represented in block 1210, points are added to the score for synergistic data and points are subtracted from the score for contradictory data, where, as mentioned above, the cumulative score associated with a detection event may indicate the confidence in the correctness of the detection.

The specific point values added or subtracted may be a matter of design for the implementer or user of the UD System. Generally, different values may be associated with different types of detectors (higher values being associated with specific as opposed to generic detectors). Different values may also be associated with different levels of confidence indicated by the detector. For example, for a generic colorimetric detector, the confidence of detection may be related to the actual change in color or intensity of the color. Within such guidelines, the particular values mentioned below were chosen based on prior experience of how well such detectors were able to assist in identifying unknown compounds.

For example, for the event of a specific colorimetric detector having a positive indication, referred to as the Main Detection Event, an initial score may be assigned based on the concentration level detected. For instance, if a molecular concentration level of less than 0.5 IDLH (immediately dangerous to life or health air concentration values as used by the National Institute for Occupational Safety and Health ("NIOSH")) is detected, then an initial score of 30 points may be assigned. Detected molecular concentration levels of between 0.5 IDLH and 1 IDLH, between 1 IDLH and 2 IDLH, and over 2 IDLH may be assigned initials scores of 40, 50 and 60 points, respectively.

In addition, the initial score may be modified depending on the type of compound indicated by the specific calorimetric detector. For example, specific detection of a nerve agent may result in 10 points being added to the initial score.

Data from each of the other specific calorimetric detectors may then be examined to determine if any indicate (e.g., in conjunction with comparison of the data in the Preloaded Database of Airborne Hazards) synergism or contradiction with the Main Detection Event. For example, if data from another specific calorimetric detector indicates the presence of a compound that is a cross reactant or potential interferent of the compound that is the subject of the Main Detection Event, then points may be added to score value. If data from another specific colorimetric detector indicates the presence of a compound that is chemically incompatible with the compound that is the subject of the Main Detection Event, then points may be subtracted from the score value and advice to re-run the test may be returned.

If desired, data from other detection equipment may be used to supplement the data from other specific colorimetric detectors. For example, if data from another specific calorimetric detector indicates the presence of a compound that, according to data from the Preloaded Database of Airborne Hazards, is a hydrolysis by-product of the compound that is the subject of the Main Detection Event, the relative humidity ("RH") may be measured (e.g., using a hygrometer). If the measured RH is consistent with hydrolysis of the compound that is the subject of the Main Detection Event, then points are added to the score value.

Data from each generic detector is also examined and for each generic detector returning data that is synergistic with the Main Detection Event, points are added to the score value. The number of points added may depend on the specific generic detector. For example, synergistic PID and FID data each may cause 15 points to be added whereas synergistic TCD, REDOX and pH data each may cause 10 points to be added.

Also, as mentioned above, detector data that is contradictory to the Main Detection Event will result in negative weights being added. For example, contradictory PID and FID data each may cause 15 points to be deducted from the score value. Similarly, contradictory TCD, pH and REDOX data each may cause 10 points to be deducted from the score value.

After the data integration of block 1210, the compound of the Main Detection Event is identified, as represented by the operations of block 1220. For example, the name of the compound of the Main Detection Event is determined based on which specific colorimetric detector had the positive indication. In addition, a confidence level is determined based on the final score associated with the Main Detection Event. For example, a score below 50 may correspond to a low confidence level and a score of 75 or above may correspond to a high confidence level.

After data for all specific calorimetric detectors having a positive indication have been processed, operation returns to block 1170 of FIG. 9 as discussed below.

Returning to FIG. 10, if the determination at block 1200 is negative (e.g., no specific colorimetric detectors gave a positive indication), then the UD System relies on only data from generic detectors to determine information related to the identity of compounds. First, data from one or more generic detectors is used to make an initial estimate of information related to the identity of the compound, as represented by the operations of block 1230. For example, positive indications from certain generic calorimetric detectors may indicate the presence of certain types of compounds, such as volatile organic compounds. Depending on the level of concentration detected, an initial score is assigned.

Next, data from other generic detectors may be examined to determine if any indicate (e.g., in conjunction with comparison of the data in the Preloaded Database of Airborne Hazards) synergism or contradiction with the initial estimate. Synergistic data results in points being added to the score and contradictory data results in points being subtracted from the score, as represented by the operations of block 1240.

A final estimate is then made of the information related to the identity of the compound, as represented in the operations of block 1250. For example, based on the final score, the final estimate may differ from the initial estimate. For instance, a final score lower than a predetermined threshold may indicate that data from the generic detectors is counter to the data in the Preloaded Database of Airborne Hazards. This could result in a final estimate of "unknown" with advice to re-run the test.

After a final estimate of information related to the identity of the compound has been made, operation returns to block 1170 of FIG. 9 as discussed below.

At block 1170, CDP Unit 9 displays the information related to the identity (e.g., specific identity or classification or "unknown") of the compounds in the air stream that it determined based on the integrated data. In addition, CDP Unit 9 may display other information such as information related to the molecular concentration level (e.g., the actual measured concentration level or categorization of the concentration level, such as "high" or "low").

The operations shown in FIGS. 9 and 10 discussed above may be further explained through the following four examples:

EXAMPLE 1

The specific colorimetric detector for nerve agent indicates a positive for a nerve agent with a high enough concentration level to result in initial score of 70 points (60 points for the high concentration level and an additional 10 points for detection of a nerve agent). Data from a hygrometer indicates a RH above 60%. No data was received from any other specific calorimetric detectors. Data from a non-specific calorimetric pH sensor indicates a slightly acidic character which is acceptable for nerve agent in RHs above 60%. Thus, the pH data from this generic detector is synergistic with the Main Detection Event thereby causing 10 points to be added to the score. Data from the PID, FID and TCD detectors are also consistent thereby causing 15, 15 and 10 points, respectively, to be added to the score. The total score is then 120 points (60+10+10+15+15+10), thereby indicating a high confidence level in the determination that a nerve agent is present.

EXAMPLE 2

The specific calorimetric detector for chlorine is triggered at high concentration, resulting in an initial score of 60 points. The specific colorimetric detector for hydrogen chloride sensor is triggered at a low concentration. Relative humidity is measured at 70%. According to data from the Preloaded Database of Airborne Hazards, chlorine can hydrolyze to form hydrogen chloride. The existence of hydrogen chloride is consistent for chlorine in the presence of high humidity. Since the data from the other specific calorimetric detector (e.g., indicating the presence of hydrogen chloride as a hydrolysis product) is synergistic with the Main Detection Event (e.g., indicating the presence of chlorine), 20 points are added. A generic pH detector indicates pH in the acidic range, which is consistent with high humidity chlorine and hydrogen chloride, so 10 points are added. A generic calorimetric redox sensor indicates the presence of a strong oxidizer, which is consistent for chlorine, so 10 points are added. There are no signals from the PID or FID detectors, but a small trigger from a TCD detector results in the addition of 5 points. The total score is then 105 points (60+20+10+10+5), thereby indicating a high confidence level in the determination that a strong chlorine oxidizer is present.

EXAMPLE 3

The specific colorimetric detector for phosgene is triggered at high concentrations, resulting in an initial score of 60 points. No data was received from any other specific colorimetric detectors. A generic redox detector indicates a strong reducing agent. This is inconsistent with the presence of phosgene since phosgene is more likely to function as an oxidizer. Since data from the generic redox detector is contradictory to the Main Detection Event, 10 points are subtracted from the score. A generic pH detector indicates a strong base, which is also inconsistent with the presence of phosgene. Consequently, 10 points are subtracted from the score. Data from the PID and FID detectors was consistent, resulting in 15 points each being added. The total score is then 70 points (60−10−10+15+15), indicating a less than high confidence level detection for phosgene. User display indicates that the test should be re-run.

EXAMPLE 4

No data is received from any specific colorimetric detectors. A generic colorimetric detector indicative of a possible volatile organic is triggered at a medium concentration level, resulting in an initial score of 10 points. The FID and PID detectors all are triggered with high concentration levels. The TCD also registers as positive. According to data from the Preloaded Database of Airborne Hazards, these are all characteristic of organic compounds. Since data from these generic detectors is synergistic with the initial estimate of a volatile organic, 15, 15 and 10 points are added to the score for the FID, PID and TCD, respectively. In addition, due to the strong readings from the PIDs, an additional 5 points are added. The total score of 55 points (10+15+15+10+5), which is a medium confidence level, results in the final estimate confirming the initial estimate—that a volatile organic compound is likely present.

As shown above, embodiments of the present invention provide numerous advantages, including but not limited to the following:

(1) Intelligent integration of a variety of different environmental sensors provides synergistic response to airborne hazards. Integration of disparate generic and specific sensors broadens selectivity of the UDS System.

(2) Due to the artificial intelligence algorithms used in UDS, the system can make assumptions about the nature of the airborne hazard, track small changes in environmental background, and trigger alarms and courses of action not possible with an unintegrated grouping of airborne hazard sensors.

(3) The UDS eliminates variation in human interpretation of colorimetric sensors by using high resolution digital optics and advanced state-of-art tracking and processing algorithms.

(4) Redundant concentration determination by comparison of both generic and specific detectors produces greater confidence in the results.

(5) Tracking algorithms allow for "refresh" assessments of environmental conditions based on continuous query of the full range of integrated sensors driven by the microprocessor tracking algorithm.

(6) Many specific detection systems can be overwhelmed by environmental interferents, the UDS is unique in that the specific calorimetric sensors have a wide dynamic range; also the large array of generic sensors also with good dynamic ranges can correct for specific sensor overwhelming by automatically restricting air flow to the more sophisticated sensors so that these sensors still remain operable even in considerable background interferences.

While the invention has been described and illustrated in connection with preferred embodiments, many variations and modifications as will be evident to those skilled in this art may be made without departing from the spirit and scope of the invention, and the invention is thus not to be limited to the precise details of methodology or construction set forth above as such variations and modifications are intended to be included within the scope of the invention. Except to the extent necessary or inherent in the processes themselves, no particular order to steps or stages of methods or processes described in this disclosure, including the Figures, is implied. In many cases the order of process steps may be varied without changing the purpose, effect or import of the methods described.

What is claimed is:

1. A system for detecting airborne hazards, comprising:
at least one computer, wherein said computer is programmed to receive both first property information and second property information for gases in an environment; and is programmed to determine the identity of an airborne hazard in said gases based on said first and second property information and a comparison of said first and second property information with data related to one or more known airborne hazards;
one or more detectors for detecting said first property information for gases from the environment; and
one or more detectors for detecting said second property information for said gases; and
wherein said data related to one or more known airborne hazards is stored in a memory of said computer; and
wherein said one or more detectors for detecting first property information include one or more colorimetric detectors, wherein said colorimetric detectors comprise a frame enclosing one or more cavities and one or more detector windows placed within said one or more cavities of said frame.

2. The system of claim 1, wherein said one or more detectors for detecting first property information further comprises one or more detectors capable of providing an indication of whether a specific compound is present.

3. The system of claim 1, wherein said one or more detectors for detecting first property information further comprises one or more detectors that measure generic chemical properties.

4. The system of claim 1, wherein at least some of said one or more detector windows include a material treated with a reagent enabling the detection of a specific compound.

5. The system of claim 1, wherein at least some of said one or more detector windows include a material treated with a reagent enabling the detection of generic chemical properties.

6. The system of claim 1, wherein said frame is a plastic card.

7. The system of claim 1, wherein said one or more detectors for detecting second property information include one or more detectors that detect ionization potential of the gases.

8. The system of claim 7, wherein said one or more detectors for detecting second property information include one or more flame ionization detectors.

9. The system of claim 1, wherein said computer is programmed to:
determine the identity of a compound in gases of an environment based on data received from one or more specific detectors;
associate a confidence level with the determination of the identity of the compound;
receive data from one or more generic detectors as to the chemical properties found in the gases;
determine whether the data received from the one or more generic detectors is synergistic with or contradictory to the determination of the identity of the compound;
increase the confidence level if the received data is determined to be synergistic with the determination of the identity of the compound; and
decrease the confidence level if the received data is determined to be contradictory to the determination of the identity of the compound.

10. The system of claim 1, further comprising said computer being programmed to:
establish a baseline for concentrations of an airborne hazard in a first gaseous environment where the concentration of the airborne hazard is known to be below a predetermined level; and
determine whether the concentrations of the airborne hazards in a second gaseous environment exceed the established baseline.

11. The system of claim 1, further comprising said computer being programmed to:
activate one or more detectors capable of specifically identifying one or more compounds in the gases if the concentration levels exceed a predetermined threshold and wherein said concentration levels are related to one or more chemical properties of gases of an environment.

12. A method for detecting airborne hazards, comprising:
receiving first property information for gases in an environment;
receiving second property information for the gases; and
determining the identity of an airborne hazard in the gases based on the first and second property information and a comparison of the first and second property information with data related to one or more known airborne hazards;
establishing a baseline for concentrations of an airborne hazard in a first gaseous environment where the concentration of the airborne hazard is known to be below a predetermined level; and
determining whether the concentrations of the airborne hazards in a second gaseous environment exceed the established baseline.

13. The method of claim 12, wherein the first property information includes the wavelength of light emitted when the gases are exposed to a reagent.

14. The method of claim 12, wherein the second property information includes the ionization potential of the gases.

15. The method of claim 12, wherein determining the identity of an airborne hazard comprises determining the specific identity of the airborne hazard.

16. The method of claim 12, wherein determining the identity of an airborne hazard comprises determining a classification for the airborne hazard.

17. A method for detecting airborne hazards, comprising:
determining the identity of a compound in gases of an environment based on data received from one or more specific detectors;
associating a confidence level with the determination of the identity of the compound;
receiving data from one or more generic detectors as to the chemical properties found in the gases;
determining whether the data received from the one or more generic detectors is synergistic with or contradictory to the determination of the identity of the compound;
increasing the confidence level if the received data is determined to be synergistic with the determination of the identity of the compound; and
decreasing the confidence level if the received data is determined to be contradictory to the determination of the identity of the compound.

18. The method of claim 17, wherein determining whether the data received from the one or more generic detectors is synergistic with or contradictory to the determination of the identity of the compound comprises comparing the received data with stored data related to one or more hazardous compounds.

19. A system for detecting and identifying airborne hazards, comprising:
one or more first colorimetric detectors capable of providing an indication of whether a specific compound is present in environmental gases;
one or more second colorimetric detectors capable of measuring generic chemical properties of environmental gases;
one or more detectors capable of measuring the ionization potential of environmental gases; and
a computer for determining the identity of an airborne hazard in the gases based on the data received from the one or more first colorimetric detectors, the one or more second calorimetric detectors, and the one or more detectors capable of measuring ionization potential.

* * * * *

UNITED STATES PATENT AND TRADEMARK OFFICE
CERTIFICATE OF CORRECTION

PATENT NO. : 7,504,958 B1
APPLICATION NO. : 11/472224
DATED : March 17, 2009
INVENTOR(S) : Genovese et al.

Page 1 of 1

It is certified that error appears in the above-identified patent and that said Letters Patent is hereby corrected as shown below:

<u>Title page,</u>
Item [75], Inventors, replace "Pazada" with --Pazda--.

Signed and Sealed this

Seventeenth Day of November, 2009

David J. Kappos
*Director of the United States Patent and Trademark Office*